(12) United States Patent
Malyugin et al.

(10) Patent No.: US 9,763,653 B2
(45) Date of Patent: Sep. 19, 2017

(54) EXPANSION RING FOR EYEBALL TISSUE

(71) Applicants: MicroSurgical Technology, Inc., Redmond, WA (US); Boris Malyugin, Moscow (RU)

(72) Inventors: Boris Malyugin, Moscow (RU); Vaclav Dusek, Bellevue, WA (US)

(73) Assignee: Microsurgical Technology, Inc., Redmond, WA (US)

( * ) Notice: Subject to any disclaimer, the term of this patent is extended or adjusted under 35 U.S.C. 154(b) by 0 days.

(21) Appl. No.: 14/732,262

(22) Filed: Jun. 5, 2015

(65) Prior Publication Data

US 2015/0265269 A1 Sep. 24, 2015

Related U.S. Application Data

(63) Continuation of application No. 13/466,968, filed on May 8, 2012, which is a continuation-in-part of
(Continued)

(51) Int. Cl.
*A61B 1/32* (2006.01)
*A61B 17/02* (2006.01)
(Continued)

(52) U.S. Cl.
CPC ............ *A61B 17/0231* (2013.01); *A61B 1/32* (2013.01); *A61F 9/007* (2013.01); *A61B 17/0218* (2013.01);
(Continued)

(58) Field of Classification Search
USPC ................ 600/201, 206, 208–210, 215, 217, 600/235–237; 623/6.42, 6.4, 6.38
See application file for complete search history.

(56) References Cited

U.S. PATENT DOCUMENTS 2,761,457 A * 9/1956 Wood ............................ 132/276
3,975,779 A 8/1976 Richards et al.
(Continued)

FOREIGN PATENT DOCUMENTS

DE 93 20 127 U1 4/1994
RU 14506 U1 2/2000
(Continued)

OTHER PUBLICATIONS

Supplementary European Search Report dated May 19, 2011 for International Application No. PCT/US08/03472, entitled "Ring Used in a Small Pupil Phacoemulsification Procedure."
(Continued)

*Primary Examiner* — Todd E Manahan
*Assistant Examiner* — Jessica Weiss
(74) *Attorney, Agent, or Firm* — Hamilton, Brook, Smith & Reynolds, P.C.

(57) ABSTRACT

A length or strand of resilient material is formed into a continuous ring having multiple tissue-engaging portions for engaging and spreading eyeball tissue segments apart. The strand is formed with elongated straight sides joined by corner portions which are enlarged in directions transverse to the length dimension of each adjacent side. The corner portions constitute the tissue-engaging portions and have top and bottom sections and a connecting section that forms a gap for receiving the tissue. Each side of the ring extends from a bottom section of one corner to a top section of an adjacent corner. When the ring is deployed, the tissue is captured in the gaps at the corners of the ring and also is engaged along each side as that side transitions from a position situated below the tissue to a position situated above the issue.

15 Claims, 11 Drawing Sheets

Related U.S. Application Data application No. 13/291,946, filed on Nov. 8, 2011, now abandoned, said application No. 13/466,968 is a continuation-in-part of application No. 12/074,731, filed on Mar. 5, 2008, now abandoned.

(60) Provisional application No. 61/411,870, filed on Nov. 9, 2010, provisional application No. 60/918,404, filed on Mar. 15, 2007.

(51) Int. Cl.
  *A61F 9/007* (2006.01)
  *A61B 17/00* (2006.01)
  *A61B 50/20* (2016.01)
  *A61B 50/30* (2016.01)

(52) U.S. Cl.
  CPC .............. *A61B 50/20* (2016.02); *A61B 50/30* (2016.02); *A61B 2017/00473* (2013.01); *A61B 2017/00526* (2013.01); *A61B 2017/00862* (2013.01)

(56) References Cited

U.S. PATENT DOCUMENTS

| | | | | |
|---|---|---|---|---|
| 4,203,168 | A * | 5/1980 | Rainin | A61F 2/16 623/6.51 |
| 4,321,916 | A * | 3/1982 | McKee | A61B 17/0231 600/209 |
| 4,387,706 | A * | 6/1983 | Glass | A61B 17/0231 600/208 |
| 4,446,582 | A | 5/1984 | Hanna | |
| 4,782,820 | A * | 11/1988 | Woods | A61B 17/0231 600/208 |
| 4,991,567 | A * | 2/1991 | McCuen, II | A61B 17/0231 600/204 |
| 5,163,419 | A * | 11/1992 | Goldman | A61B 17/0231 600/206 |
| 5,267,553 | A * | 12/1993 | Graether | A61B 17/0231 600/236 |
| 5,299,564 | A * | 4/1994 | Sabatino | A61B 17/0231 600/236 |
| 5,318,011 | A | 6/1994 | Federman et al. | |
| 5,322,054 | A * | 6/1994 | Graether | A61B 17/0231 269/303 |
| 5,334,217 | A * | 8/1994 | Das | A61B 17/0057 606/151 |
| 5,374,272 | A * | 12/1994 | Arpa | A61F 9/007 600/236 |
| 5,441,045 | A | 8/1995 | Federman | |
| 5,489,295 | A | 2/1996 | Piplani et al. | |
| 5,693,085 | A * | 12/1997 | Buirge et al. | 623/1.13 |
| 5,951,565 | A * | 9/1999 | Freeman | A61F 2/1605 606/107 |
| 6,068,643 | A * | 5/2000 | Milverton | A61F 9/007 606/107 |
| 6,200,336 | B1 * | 3/2001 | Pavcnik | A61F 2/07 623/1.13 |
| 6,231,583 | B1 * | 5/2001 | Lee | A61F 9/007 606/151 |
| 6,497,724 | B1 | 12/2002 | Stevens et al. | |
| 6,620,098 | B1 | 9/2003 | Milverton | |
| 6,814,748 | B1 | 11/2004 | Baker et al. | |
| 7,412,993 | B2 | 8/2008 | Tzeng | |
| 7,985,180 | B2 | 7/2011 | Brown | |
| 8,323,296 | B2 * | 12/2012 | Malyugin | A61B 17/0231 606/107 |
| 8,496,583 | B1 * | 7/2013 | Reynard | A61B 17/0231 600/235 |
| 8,900,136 | B2 * | 12/2014 | Cote | A61F 9/00736 600/208 |
| 9,089,397 | B2 * | 7/2015 | Clarke | A61F 9/04 |
| 9,504,459 | B1 * | 11/2016 | Nallakrishnan | A61B 17/0231 |
| 2003/0092970 | A1 * | 5/2003 | Lee | A61B 17/0231 600/236 |
| 2008/0108879 | A1 * | 5/2008 | Brown | A61B 17/0231 600/236 |
| 2008/0243139 | A1 * | 10/2008 | Dusek | A61B 17/0231 606/107 |
| 2008/0269888 | A1 | 10/2008 | Malyugin | |
| 2008/0275461 | A1 * | 11/2008 | Nallakrishnan | A61F 9/0008 606/107 |
| 2012/0136322 | A1 * | 5/2012 | Alster | A61F 9/0017 604/290 |
| 2012/0289786 | A1 * | 11/2012 | Dusek | A61B 17/0231 600/236 |
| 2013/0053860 | A1 | 2/2013 | Malyugin | |
| 2013/0096386 | A1 * | 4/2013 | Christensen | A61B 17/0231 600/206 |
| 2013/0131458 | A1 * | 5/2013 | Malyugin | A61B 1/32 600/236 |
| 2013/0267988 | A1 * | 10/2013 | Sussman | A61B 17/0231 606/198 |
| 2013/0331939 | A1 * | 12/2013 | Stevens | A61F 2/16 623/6.51 |
| 2014/0221759 | A1 * | 8/2014 | Mackool | A61B 17/0231 600/209 |
| 2014/0378773 | A1 * | 12/2014 | Dykes | A61B 17/0293 600/208 |
| 2015/0164685 | A1 * | 6/2015 | Bhattacharjee | A61B 17/0231 606/198 |

FOREIGN PATENT DOCUMENTS

| | | |
|---|---|---|
| RU | 14505 U1 | 9/2000 |
| WO | WO 95/15120 A1 | 6/1995 |
| WO | WO 00/32141 A1 | 6/2000 |
| WO | WO 2008/115455 A1 | 9/2008 |

OTHER PUBLICATIONS

International Search Report and Written Opinion dated Jul. 23, 2008 for International Application No. PCT/US08/03472, entitled "Ring Used in a Small Pupil Phacoemulsification Procedure."

International Preliminary Report on Patentability dated Sep. 15, 2009 for International Application No. PCT/US08/03472, entitled "Ring Used in a Small Pupil Phacoemulsification Procedure."

Cimberle, M., "New Pupil Expander Easier to Implant, Gentle on the Iris," *Ocular Surgery News Europe Asia Edition*, [online], May 2006 [retrieved on Mar. 27, 2013]. Retrieved from the Internet URL: http://www.osnsupersite.com/view.aspx?rid=16863.

Office Communication, U.S. Appl. No. 13/466,968, filed May 8, 2012, entitled "Expansion Ring For Eyeball Tissue", Date of Communication: Dec. 1, 2014.

Office Communication, U.S. Appl. No. 13/466,968, filed May 8, 2012, entitled "Expansion Ring For Eyeball Tissue", Date of Communication: Jun. 30, 2015.

Office Communication, U.S. Appl. No. 13/661,982, filed Oct. 26, 2012, entitled "Ring Used in a Small Pupil Phacoemulsification Procedure", Date of Communication: Feb. 20, 2015.

Office Communication, U.S. Appl. No. 13/661,982, filed Oct. 26, 2012, entitled "Ring Used in a Small Pupil Phacoemulsification Procedure", Date of Communication: Nov. 25, 2015.

Office Communication, U.S. Appl. No. 13/661,982, filed Oct. 26, 2012, entitled "Ring Used in a Small Pupil Phacoemulsification Procedure", Date of Communication: Oct. 18, 2016.

Office Communication, U.S. Appl. No. 13/661,982, filed Oct. 26, 2012, Date of Communication: Apr. 6, 2016.

He et al., "Distribution and Heritability of Iris Thickness and Pupil Size in Chinese: The Guarngzhou Twin Eye Study", IOVS ARVO Journal, vol. 50, Issue 4, pp. 1593-1597, Apr. 2009.

* cited by examiner

EXPANSION RING FOR EYEBALL TISSUE

RELATED APPLICATIONS

This application is a continuation of U.S. application Ser. No. 13/466,968, filed May 8, 2012, which is a continuation-in-part of U.S. application Ser. No. 13/291,946 filed Nov. 8, 2011; which claims the benefit of U.S. provisional application 61/411,870 filed Nov. 9, 2010 and is a continuation-in-part of U.S. application Ser. No. 12/074,731 filed Mar. 5, 2008; which claims the benefit of U.S. Provisional Application No. 60/918,404 filed Mar. 15, 2007. The entire teachings of the above applications are incorporated herein by reference.

BACKGROUND OF THE INVENTION

The present invention relates to a ring used to maintain an opening in eyeball tissue in an expanded condition during an ophthalmic procedure.

During ophthalmic surgery, it is sometimes desirable to enlarge an opening in eyeball tissue, such as holding the iris open for access through the pupil. For example, cataracteous lenses can be replaced in a procedure commonly referred to as phacoemulsification, or "phaco" for short. In a phaco procedure access through the pupil is required to insert and manipulate an ultrasonically driven tool to break apart and aspirate the lens. It has been proposed that, at least in some cases, expansion of the opening be achieved mechanically by hooks that engage and pull against edge portions of the eyeball tissue, such as inner edge portions of the iris to expand the pupil during a phaco procedure. See, for example, the hooks disclosed in U.S. Pat. No. 5,716,328.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

The present invention provides a length or strand of resilient material formed into a continuous ring having multiple tissue-engaging portions for engaging and spreading eyeball tissue segments apart. The strand is formed with elongated straight sides joined by corner portions which are enlarged in directions transverse to the length dimension of each adjacent side. The corner portions constitute the tissue-engaging portions and have top and bottom sections and a connecting section that forms a gap for receiving the tissue. Each side of the ring extends from a bottom section of one corner to a top section of an adjacent corner. When the ring is deployed, the tissue is captured in the gaps at the corners of the ring and also is engaged along each side as that side transitions from a position situated below the tissue to a position situated above the issue.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Figure 1:
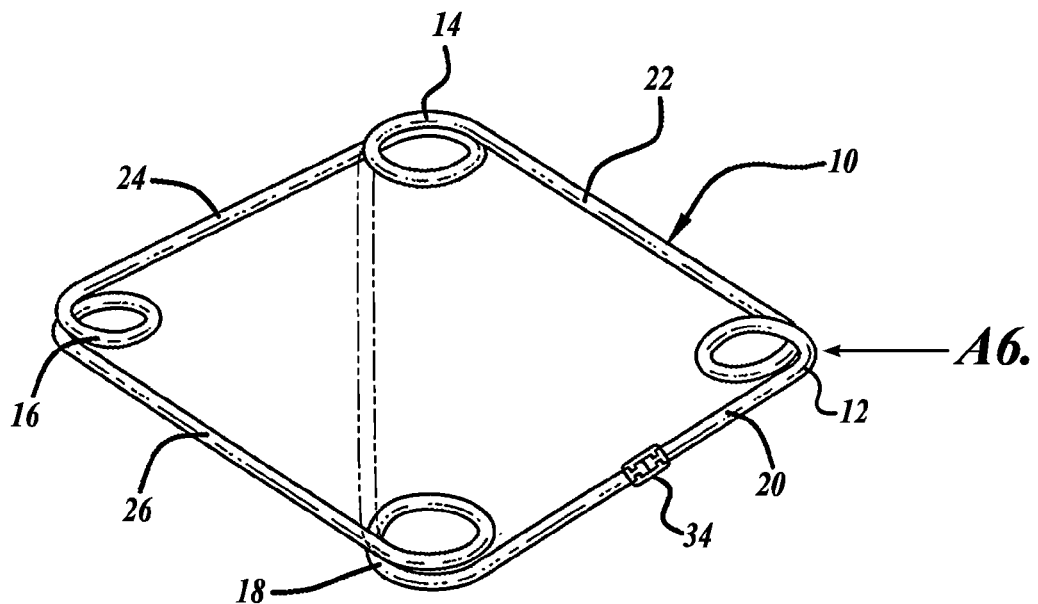
FIG. 1 is an enlarged, diagrammatic top perspective of an expansion ring in accordance with the present invention.

In the embodiment of the present invention shown in FIG. 1, a continuous ring 10 is formed from a single long strand of resilient material, such as a molded plastic material. In the illustrated embodiment, the ring 10 has four corners 12, 14, 16, and 18 connecting four straight sides 20, 22, 24, and 26. As described in more detail below, each corner is formed by a loop of the strand. Although a square ring is illustrated, it is to be understood that the ring may have a rectangular configuration, or a nonrectangular shape. For example, the ring may be formed as a triangle that has three sides and three loops located at the ring corners, as represented by the broken line in FIG. 1 representing a triangular ring having corners 12, 18, and 14.

Figure 2:
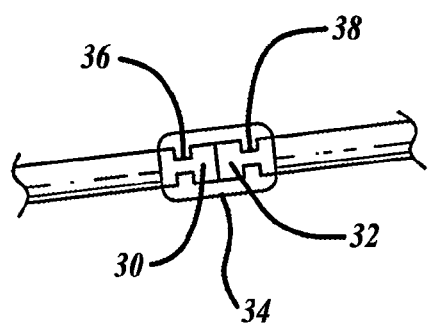
FIG. 2 is a further enlarged, fragmentary detail thereof.

FIG. 2 shows a preferred construction in which the ring is formed from one length of material with two ends 30 and 32 that are "butt attached" by adhesive represented at 34. Each of the ends 30 and 32 has an indent 36, 38, respectively, such that the adhesive 34 can flow into the indents to increase the strength of the butt attachment. The indents create surface structure that minimizes shearing and de-lamination of the adhesive 34 from the ring 10. A representative adhesive is a Class VI epoxy, applied by a tool that ensures a repeatable volume and dimension of the solidified adhesive form.

Figure 3:
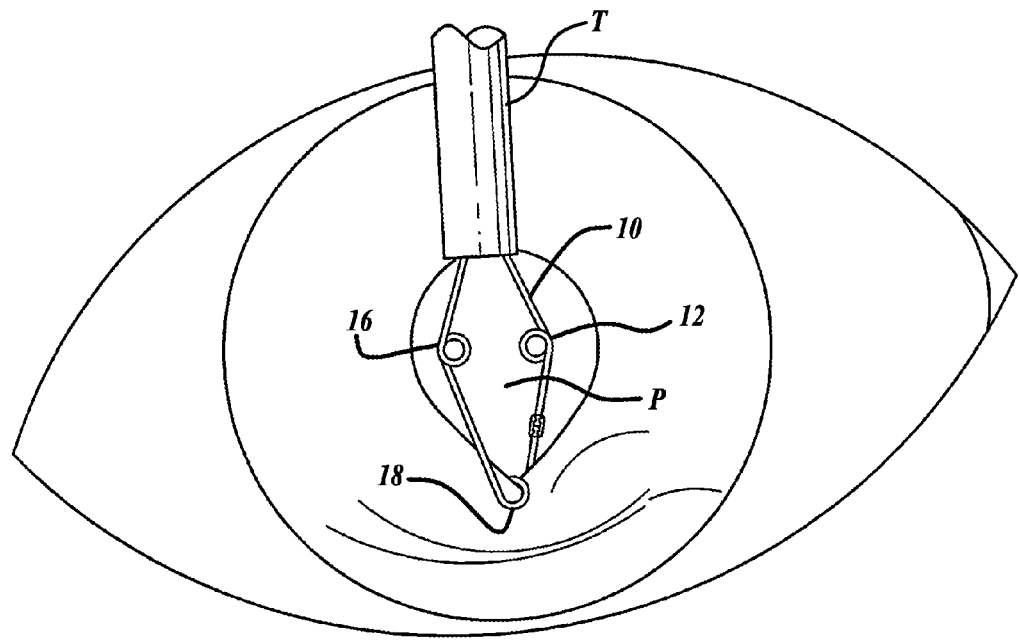
FIG. 3 is a diagrammatic top plan thereof.
Figure 4:
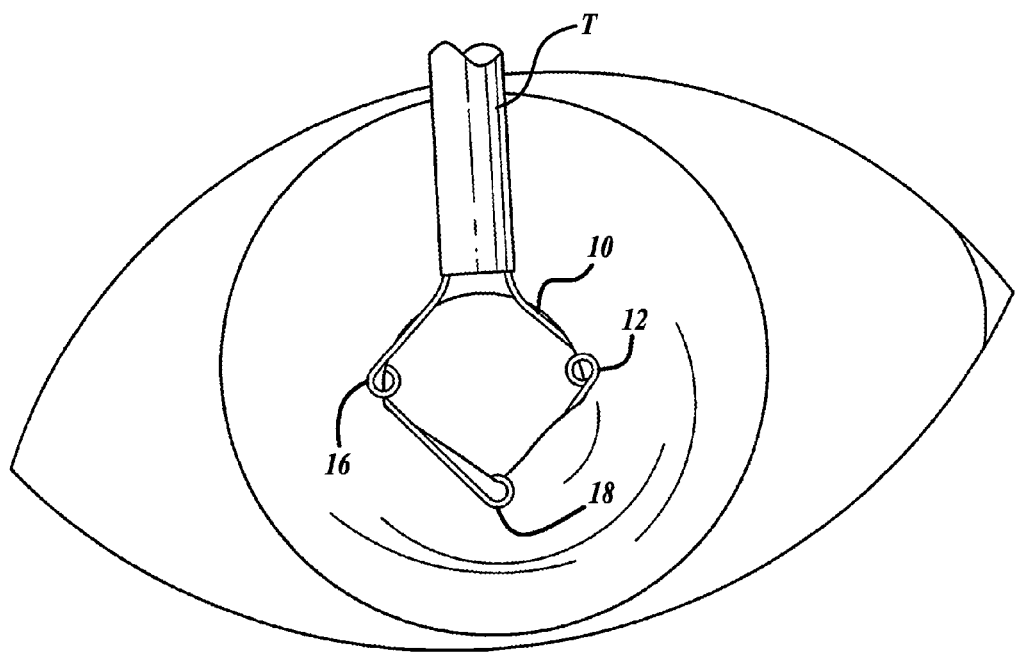
FIG. 4 is a diagrammatic top plan thereof corresponding to FIG. 3 but with parts in different positions.
Figure 5:
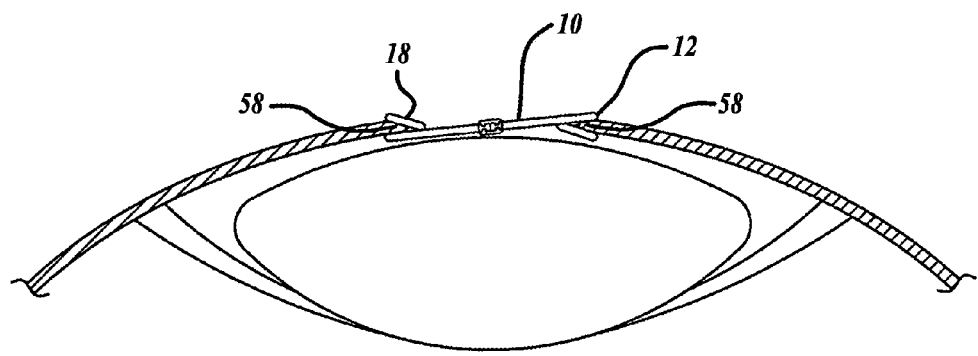
FIG. 5 is a diagrammatic side elevation thereof.

With reference to FIGS. 3-5, the ring 10 can be drawn into an insertion tube T and, after insertion of the tube into the posterior chamber of the eye, projected from the tube and manipulated to expand the opening of the iris. FIG. 3 shows the initial stages of the ring 10 being inserted into the pupil P. The corner loop 18 remote from the tube is manipulated to capture an edge portion of the iris. Corners 12 and 16 at the sides form deflection areas or "hinges" between the sides adjacent to them. With reference to FIG. 4, as the ring is inserted farther it can be manipulated so that iris tissue is received in such side loops 12 and 16. As seen in FIG. 5, each corner loop has a gap 58 that receives and captures iris tissue. The loop design provides an easy means of inserting and capturing iris tissue.

Figure 6:
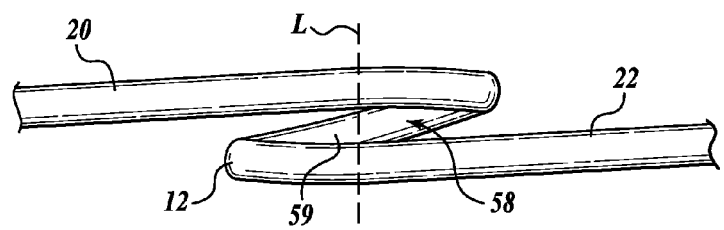
FIG. 6 is an enlarged, fragmentary detail of a corner portion thereof viewed generally in the direction indicated by the arrow A6 in FIG. 1 and showing such corner portion in elevation looking toward the center of the ring.
Figure 7:
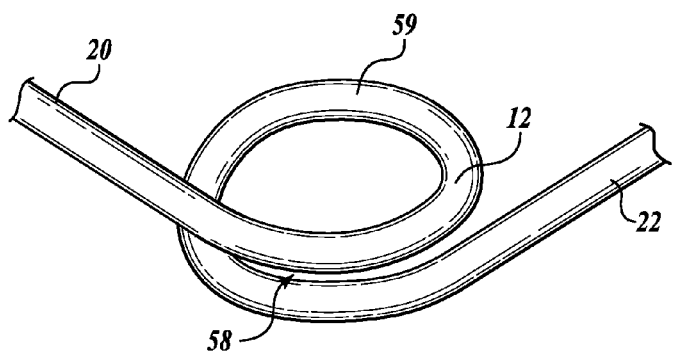
FIG. 7 is an enlarged, fragmentary detail of such corner portion corresponding to FIG. 6 but showing such corner portion in an oblique orientation.

More specifically, FIG. 6 is an enlarged elevation view looking inward toward the center of the ring at corner 12, and FIG. 7 is a corresponding view but at an oblique angle from a higher viewpoint. Although corner 12 is referenced, all four corners are identical, as shown in the drawings. Each corner connects two adjacent straight sides, each long and narrow and elongated in the direction of its length (which can be referred to as the "x" dimension). For corner 12, the adjacent sides connected are side 20 which is inclined up from the bottom of corner 18 (see FIG. 1) to the top of corner 12. Similarly, side 22 is inclined away from the bottom of corner 12 to the top of corner 14 (FIG. 1), and so on around the ring. Each side extends from the bottom of one corner to the top of another, and each corner is enlarged in a first direction transverse to the x dimension of a side it connects (which can be referred to as the "y" dimension; vertical in the orientation of FIG. 6). The broken line L in FIG. 6 represents the location of the outermost point of the corner where the widest part of the gap 58 is located (and where the corner is presented to the tissue to be captured). From line L the corner loop has an arcuate section 59 that spirals down and to the inside of the ring like a single loop or coil of a helix. As compared to the x and y dimensions, the inward direction can be referred to as the "z" dimension (which is into the page in the orientation of FIG. 6, and which is orthogonal to the y dimension). The corner is enlarged in the y and z dimensions as compared to the narrow height and width of a side. As seen in FIG. 6, the inner part of the section 59 will extend diagonally along the edge of the tissue captured in the gap 58 resulting in a broad contact area at the edge of the iris, for example. The gap 58 can be proportioned such that there is a clamping force applied to the iris tissue captured in the corner loop.

As represented diagrammatically in FIG. 4, the iris is expanded further as the ring is inserted and the corners capture the edge of the iris and spread it open, providing a larger space for an ophthalmic procedure to be performed.

Figure 8:
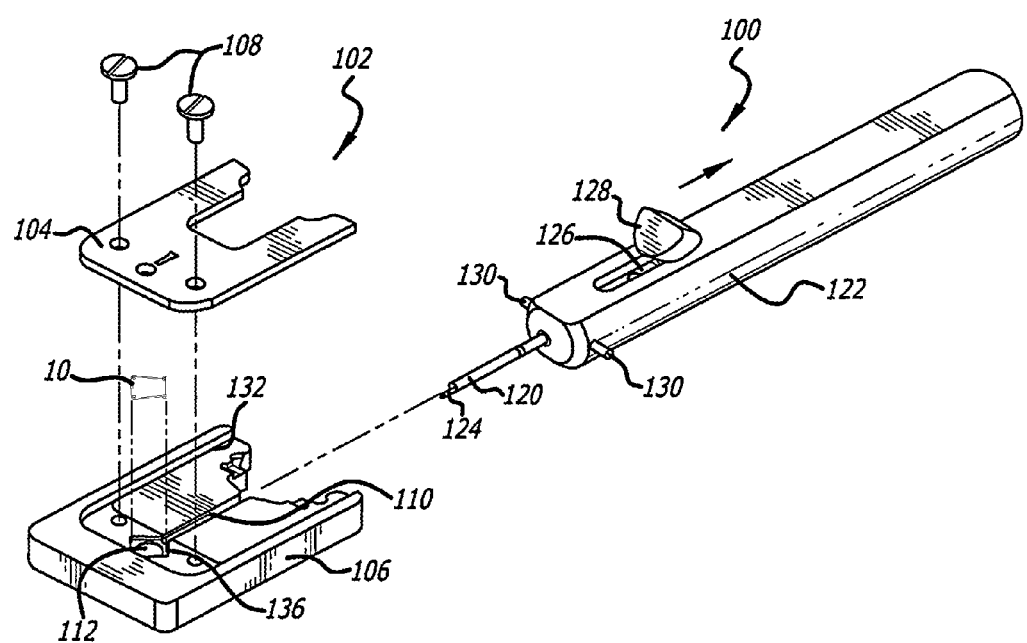
FIG. 8 is a perspective of an injector and ring holder that can be used to load and inject the ring, with some parts shown in exploded relationship.

FIG. 8 shows an embodiment of an injector 100 that can be used to inject a ring 10 into a patient's eye. The ring can be loaded into the injector with the use of a holder 102. The holder 102 may include a cover 104 that is attached to a base plate 106 by fasteners 108. The base plate 106 has a channel 110 and a recess 112. The recess 112 receives the ring 10.

The injector includes a cannula 120 attached to a handle 122. Within the cannula 122 is a wire hook 124. The wire hook 124 is connected to an inner slide tube 126 located within the handle 122. A button 128 is attached to the inner slide tube 126. The injector 100 may also have a pair of guide pins 130 that are attached to the handle 122 and cooperate with the corresponding channel features 132 of the base plate 106 to properly align the injector 100 when the cannula is inserted into the base plate channel 110.

In operation, the cannula 120 is inserted into the base plate channel 110. When fully inserted the wire hook 124 extends into the ring 10. The cover 104 may have an opening that allows an operator to visually see the hook 124. An operator pulls the button 128 in the direction indicated by the arrow. Pulling the button 128 causes the hook 124 to grasp the ring at a corner loop and pull the ring into the cannula 120. The recess 112 has tapered walls 136 to assist in the ring collapsing within the channel 110 for insertion into the cannula 120. Once loaded, the ring 10 can be injected into a patient's eye by pushing the button 128 in the opposite direction.

Figure 9:
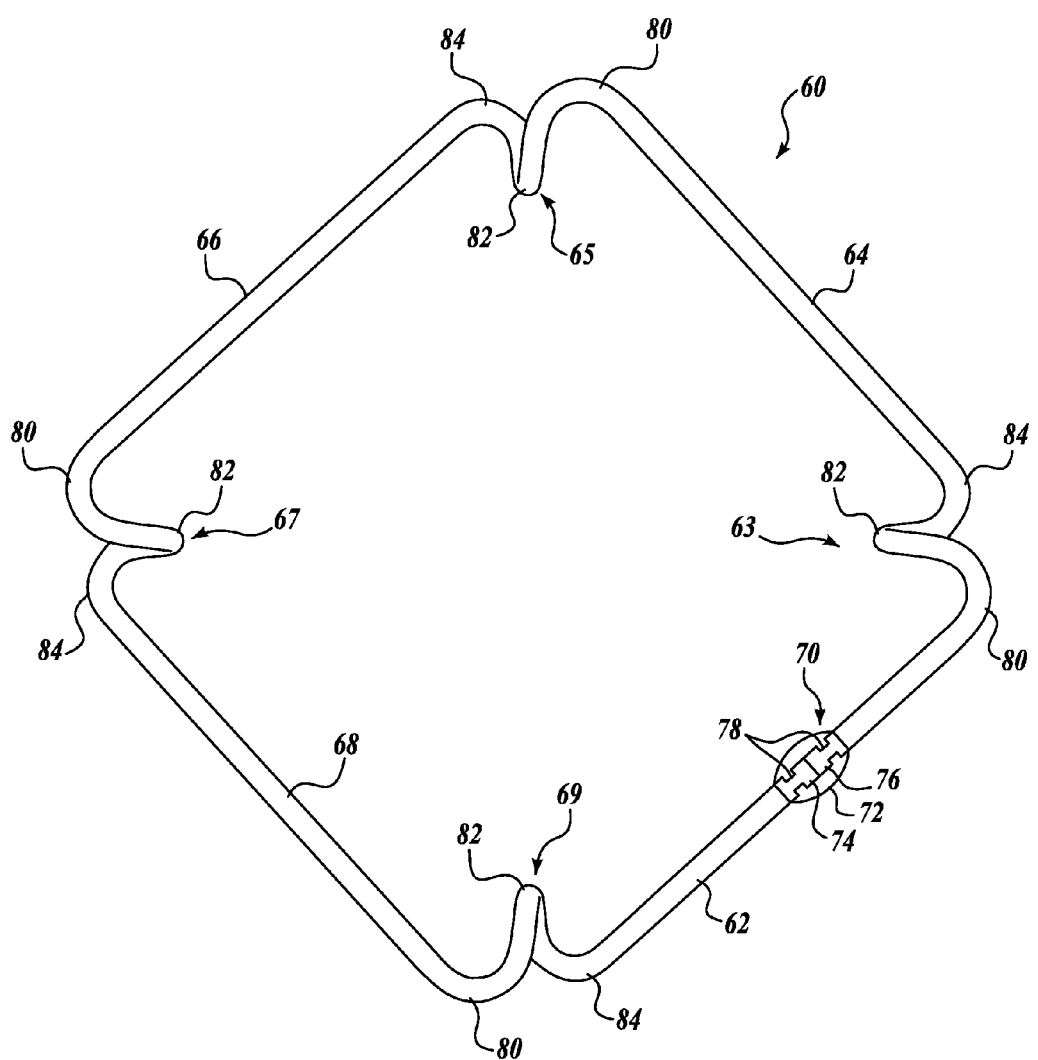
FIG. 9 is a diagrammatic top plan of a modified expansion ring in accordance with the present invention.

FIG. 9 shows a modified iris extension ring 60 in accordance with the present invention. It should be noted that in FIG. 9, and all drawings, sizes are exaggerated for ease of illustration and understanding. Ring 60 is formed from a single long strand of resilient material such as 4-0 or 5-0 polypropylene surgical suture. The ring material has memory characteristics such that when held taut in a desired shape and then heat treated and cooled, such shape will be retained in the relaxed or "at rest" state. Due to the resiliency of the material, from the relaxed state the material can be deformed, in which case it applies a resisting force tending to return to the preformed shape.

In the case of the embodiment of the present invention shown in FIG. 9, ring 60 has four straight sides 62, 64, 66, and 68. Side 62 has the end butt joint 70 where a drop of adhesive 72 secures the ends 74, 76, such ends preferably having the indented portions 78 to increase the holding effectiveness of the adhesive.

In the plan view of FIG. 9, side 64 is perpendicular to side 62. These sides are joined by a corner portion 63 which has three distinct bends, namely, a first obtuse bend 80 (essentially 135.degree. inward and to the left as viewed in FIG. 9), a second return bend 82 (essentially 180.degree. inward and then down away from the viewer and then toward the right as viewed in FIG. 9), and a third obtuse bend 84 (essentially 135.degree. up and to the left as viewed in FIG. 9). Corner 65 joining sides 64 and 66 is identical to corner 63 with the three distinct portions 80, 82, 84, as are the two additional corner portions 67 (joining sides 66 and 68) and 69 (joining sides 68 and 62).

Figure 10:
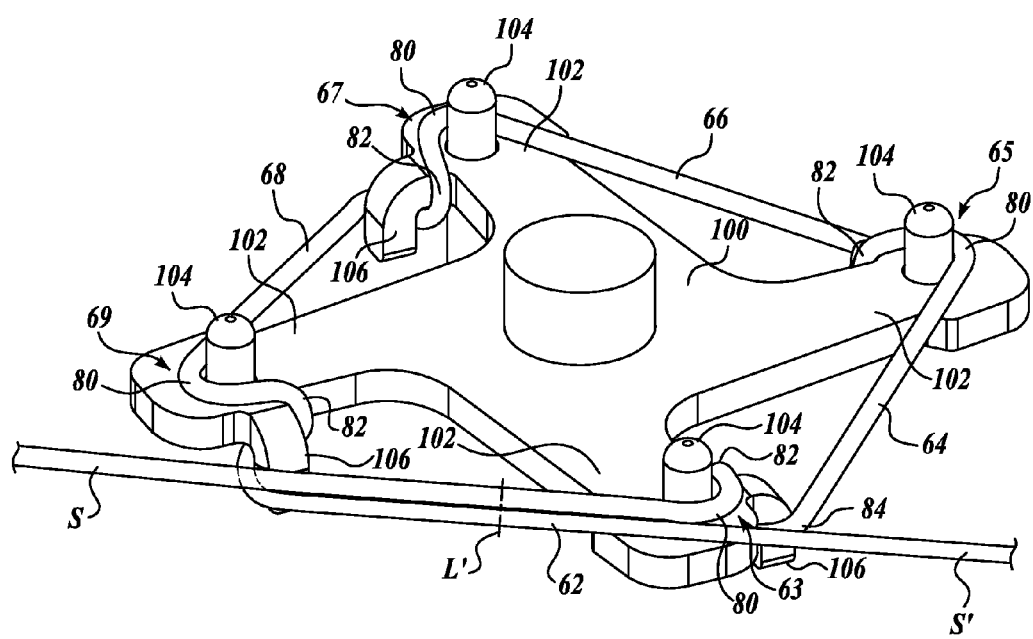
FIG. 10 is a diagrammatic top perspective thereof during manufacture.

The shape of the ring embodiment 60 can be achieved by use of a winding fixture, aspects of which are shown diagrammatically in FIG. 10. The fixture includes a composite jig having a thin plate 100 with four generally radially extending arms 102 spaced 90.degree. apart. Vertical pins 104 extend upward through holes in the outer end portions of the arms 102 at locations corresponding to the obtuse bends 80. The end portions of the arms 102 also have short tabs 106 curved down from the plane of the remainder of the plate 100, approximately aligned with the pins 104.

Aspects of the ring 60 may be better appreciated in conjunction with the manner in which the ring is manufactured. Starting at the left of FIG. 10, a length of the suture material S is stretched to the lowermost pin 104 and wound around the outer periphery of the pin to achieve the inward obtuse bend 80 of approximately 135.degree. for the corner portion 63. From there the suture extends along the top of the plate 100 to the inner edge of the associated tab 106, then down under the plate and back outward to form the inner bend 82 of approximately 180.degree. This section of the suture extends along the face of the tab adjacent to the corresponding arm 102 and then along the outer edge of tab and toward the next pin 104 to form the last obtuse bend 84 of corner portion 63. Thus, there is a short stretch of suture that extends almost radially along the face of the tab and the obtuse bend 84 which leads to the side 64. The winding procedure is the same at corner portions 65, 67, and 69, with the opposite ("exiting") end portion S' of the length of suture extending to the right as seen in FIG. 10, along side the entering portion S.

Figure 11:
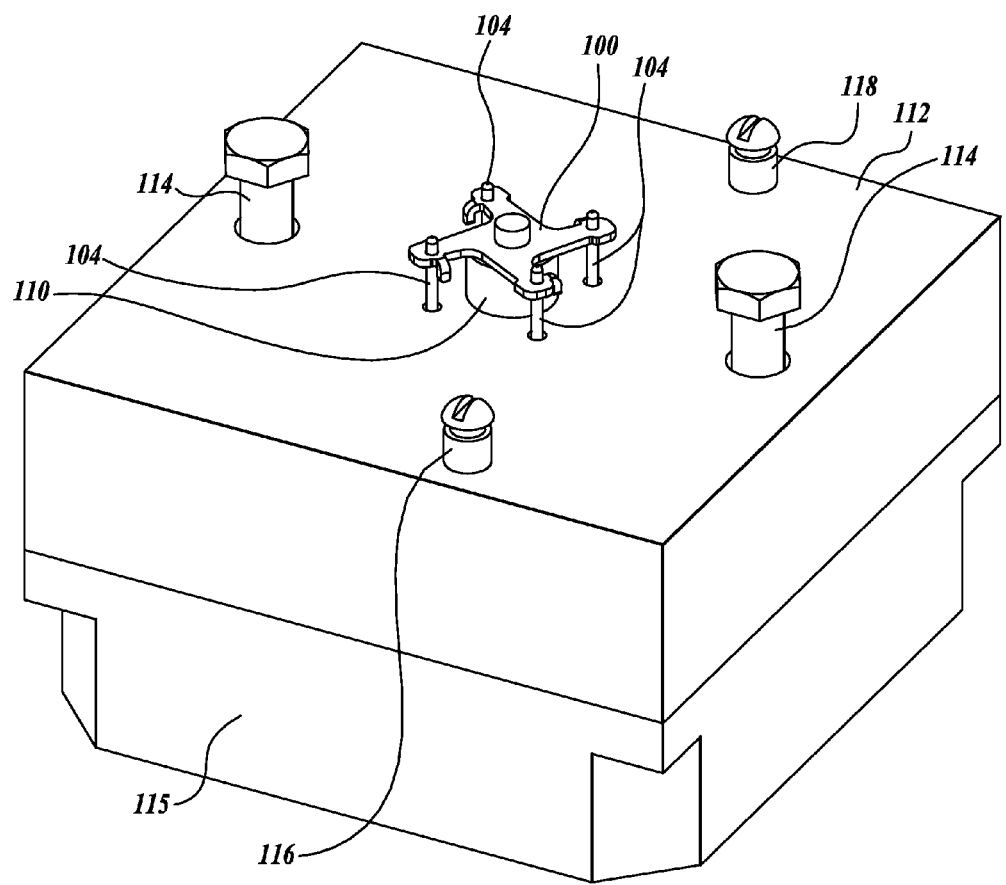
FIG. 11 is a diagrammatic top perspective of manufacturing equipment therefore.

FIG. 11 shows the winding fixture on a smaller scale (dimensions still exaggerated due to the extremely small nature of the ring, particularly the suture which may be on the order of 0.006 to 0.008 inch diameter). Plate 100 is mounted on a central hub 110 fixed to an upper elevator block 112. Block 112 is guided for vertical movement by bolts 114 and the pins 104 that extend somewhat loosely through the elevator block 112 to a base block 115. An entrance screw 116 is provided to anchor the stretch of suture that leads to the winding pins, and an exit screw 118 is used to anchor the opposite or exiting end portion of the suture after the winding operation is completed (i.e., after the suture is routed as shown in FIG. 10). With the suture thus held in the desired form, it is heated in an oven to close to the softening temperature for a period of time sufficient to achieve the desired memory characteristics. In a representative embodiment, the heat treating can be at a temperature of 165.degree. C. to 170.degree. C. for 6 to 8 minutes, but the temperature and time may be adjusted depending on the particular material used. Thereafter, the fixture and iris extension ring contained thereon are cooled.

Figure 12:
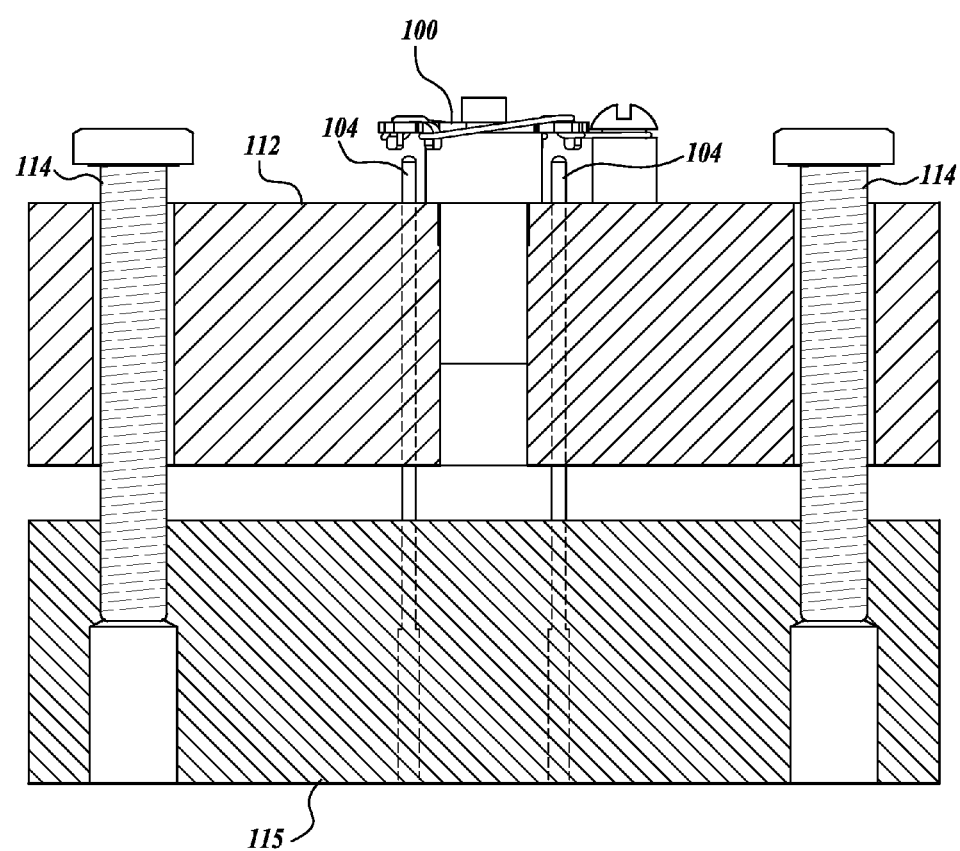
FIG. 12 is a diagrammatic section of the manufacturing equipment therefore.

With reference to FIG. 10, after cooling, the entering and exiting stretches of suture can be severed in one snip, preferable approximately midway between the adjacent corners, such as at the location indicated by the broken line L' in FIG. 10. Then, as represented in FIG. 12, the upper elevator block 112 is raised such that the winding plate 100 is lifted to a position above the tops of the pins 104, which simplifies removal of the ring 60 from the fixture, prior to completion of the ring by joining the cut ends as previously described.

Figure 13:
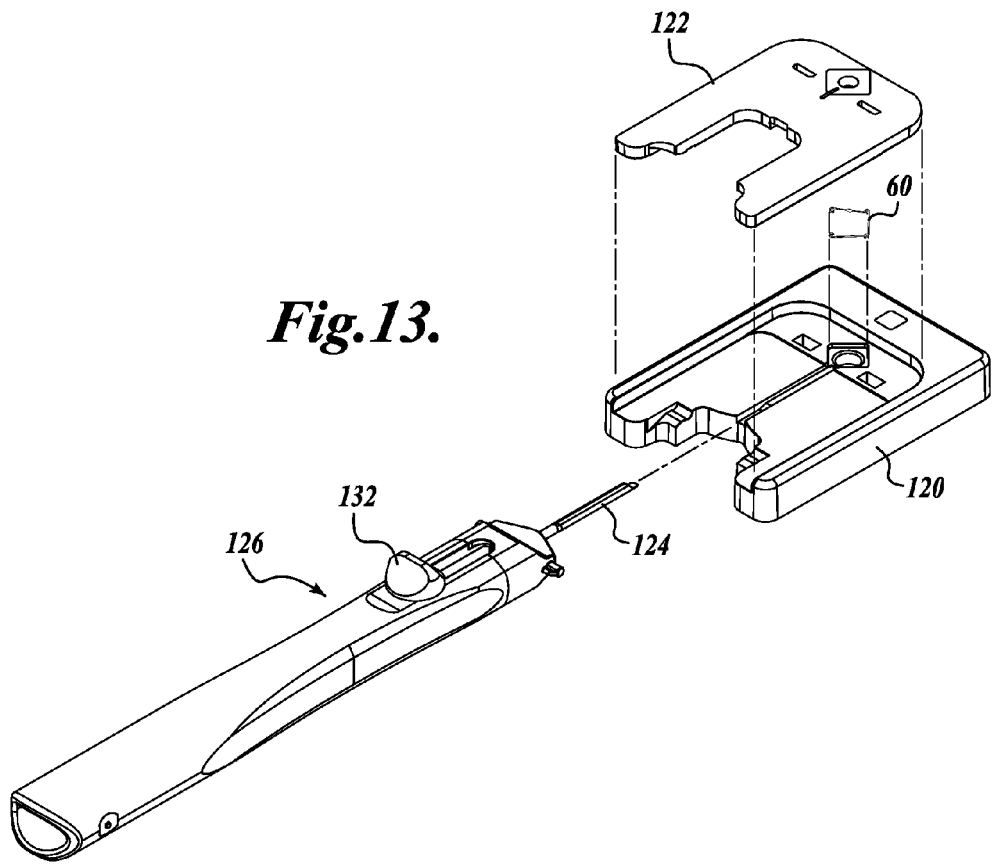
FIG. 13 is a diagrammatic top perspective of equipment for insertion thereof.
Figure 14:
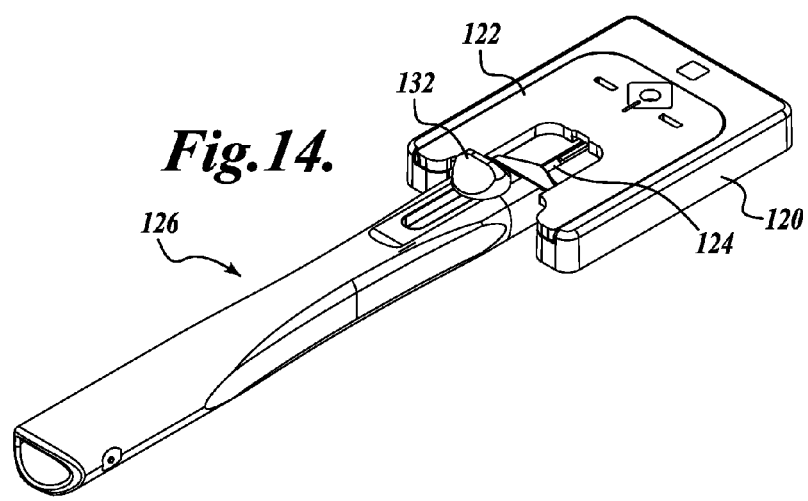
FIG. 14 is a diagrammatic top perspective of equipment for insertion thereof corresponding to FIG. 13 but with parts in different positions.

With reference to FIG. 13, a single completed ring 60 can be fitted in a recess of a holder having a bottom section 120 and lid section 122. Such holder has a channel leading to the recess in which the ring 60 is positioned, for reception of the insertion tube 124 of an implanting instrument 126. FIG. 14 illustrates the parts connected with the insertion tube received in the channel.

Figure 15:
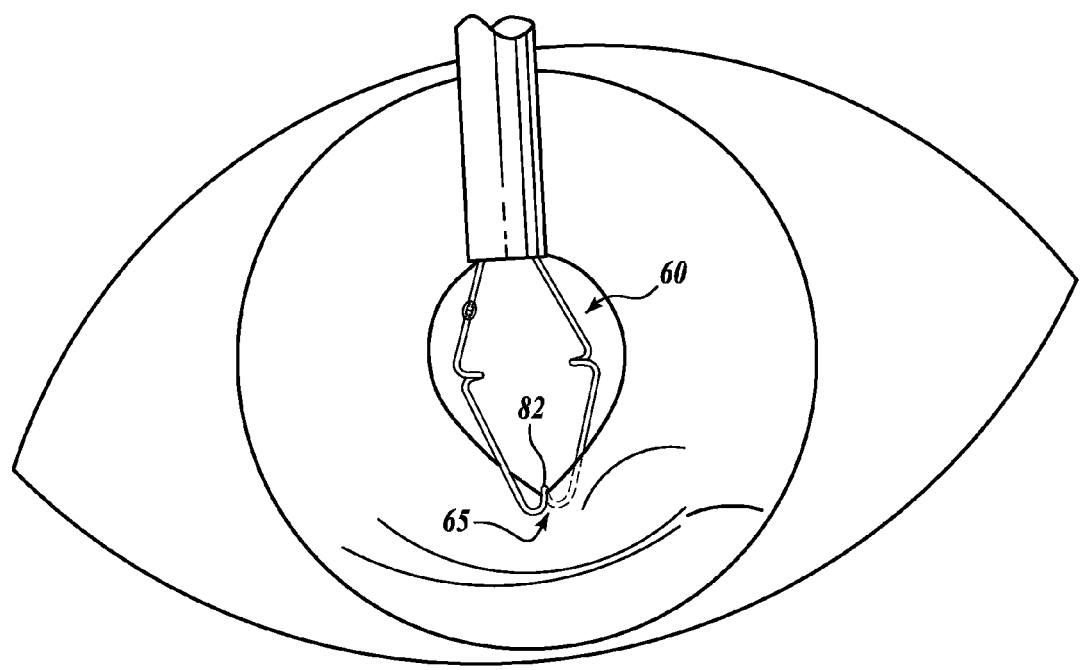
FIG. 15 is a diagrammatic top plan illustrating insertion thereof.
Figure 16:
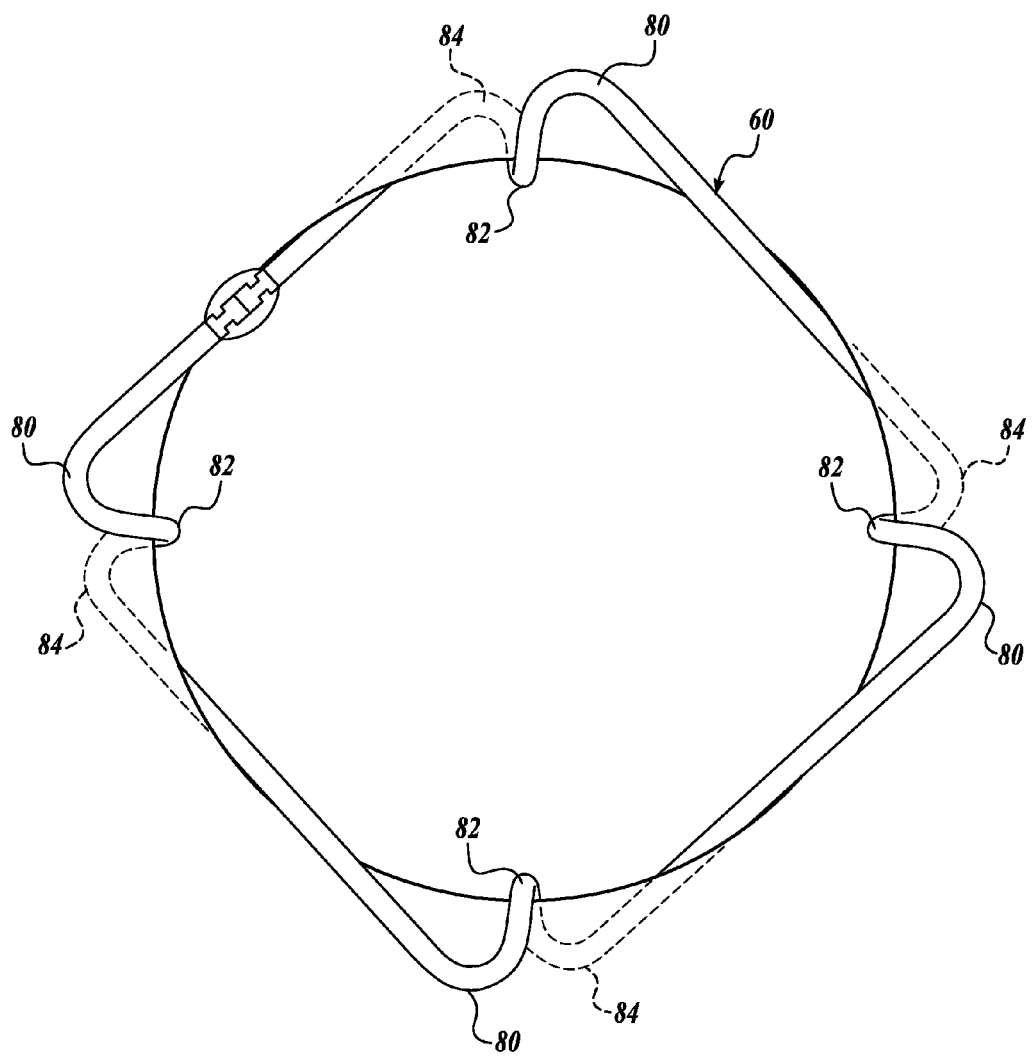
FIG. 16 is a diagrammatic top plan illustrating aspects thereof after insertion.

FIG. 15 illustrates ejecting of the ring 60 in the eye, with the inner bend 82 of corner portion 65 engaged against an edge portion of the iris. Such edge portion rides into the gradual arc of bend 82 with little or no friction that could cause abrasion. Each corner is enlarged in two directions transverse to the length (x dimension) of each narrow strand side that it connects. One transverse direction (y dimension) forms the gap or opening presented to the tissue to be captured. The other transverse direction (z dimension) extends inward and limits the extent of insertion of the tissue into the channel or pocket formed by the inner portion (bend 82 for this embodiment) of the corner. FIG. 16 illustrates the position after the ring 60 has been fully deployed. The innermost bend 82 of each of the corner portions receives a portion of the inner edge of the iris. The ring is sized such that it is in a slightly compressed state when deployed, so that an expansion force is applied against the iris to increase the opening. Also, it can be seen in FIG. 16 that the bends 82 do not apply the only edge-contacting portions of the ring. A top obtuse bend 80 at each corner leads to the corresponding return bend 82. Such return bend 82, in turn, leads to a bottom obtuse bend 84 (shown in broken lines). The side to which a bottom obtuse bend 84 leads is inclined upward (outward) slightly due to the positioning of the suture on the winding fixture, just as the straight sides of the previously described embodiment transition from the bottom of one corner to the top of the next, and each side of the ring emerges from the pupil approximately midway between adjacent bends (or corners), or at least somewhat centrally between the bends. Thus, there are eight spaced points of contact of the iris edge portion by the contracted ring 60 (or ring 10) for a more even application of an expanding force.

As seen in FIG. 16 ring 60 can be formed with no parts of any corner that directly overlie one another. The dimensions of the ring and the various bends are chosen so that minimal abrasive force is applied to the iris, and no or essentially no pinching or clamping force. However, the bends 82 do not extend diagonally across the inner edge of the iris as in the previously described embodiment. Dimensions are selected such that the opening formed by each return bend 82 is at least as great as the marginal thickness of the iris, with no coils or loops located one above the other.

More specifically, it can be seen in FIG. 10 that each obtuse bend 80 (best seen for the bend 80 at the top of the view) is angled outward slightly from its pin 104 to the corner between the plate arm 102 and the corresponding tab 106 where the central portion of the return bend 82 is formed. The bottom part of such return bend is canted slightly away from the top part of the bend to the outer edge of the tab. The radius of curvature of the return bend is determined primarily by the thickness of the plate 100. In a representative embodiment, the plate can be 0.015" thick. It has been found, however, that the total depth of the channel or notch formed by the return bend will be somewhat greater than the plate thickness, such as 0.019" to 0.020" in a representative embodiment.

While illustrative embodiments have been illustrated and described, it will be appreciated that various changes can be made therein without departing from the spirit and scope of the invention.

What is claimed is:

1. An expansion device for an iris of a patient's eyeball to mechanically maintain the pupillary margin of the iris in a desired open condition for surgical access through the pupil defined thereby during an ophthalmic procedure, said expansion device comprising a strand of resilient material formed into an unfolded ring having a central opening, such ring having: multiple tissue-engaging portions spaced apart around the ring, each tissue-engaging portion having a gap or notch providing an outward opening for reception of a pupillary marginal portion of the iris; and elongated sides extending between the tissue-engaging portions;

the ring being sized for reception in an iris of a patient and the gaps or notches of the tissue-engaging portions being constructed and arranged for capturing and spreading apart pupillary marginal portions of the iris to enlarge the pupil defined by the iris, each of the elongated sides having a trailing portion extending from one tissue-engaging portion and a leading portion extending to another tissue-engaging portion, each tissue-engaging portion having an arcuate connecting section of the strand extending between and joining the leading portion of one side and the trailing portion of another side, wherein the connecting section of each tissue-engaging portion is a single loop of the strand spiraled inward from adjacent sides of the ring, each connecting section being shaped to form the gap or notch of its tissue-engaging portion and sized to receive and capture a pupillary marginal portion of the iris therein, whereby, when the ring is deployed in the iris with pupillary marginal portions of the iris captured in the gaps or notches, the ring mechanically maintains the iris in a desired open condition.

2. The device defined in claim 1, in which each tissue-engaging portion of the ring is formed at a corner between two sides of the ring and has a top and a bottom spaced apart from each other so as to form the gap or notch.

3. The device defined in claim 2, in which each side of the ring extends between the bottom of one corner and the top of another of the corners, whereby, when the ring is deployed with pupillary marginal portions of the iris captured in the gaps or notches of adjacent corner portions, each side transitions across the pupillary margin of the iris between two of the tissue-engaging portions.

4. The device defined in claim 1, in which the loop is helical.

5. The device defined in claim 1, in which the loop has overlapping portions at an outer edge portion of the corresponding tissue-engaging portion to overlie and underlie the inner edge of an iris, respectively.

6. The device defined in claim 1, in which the connecting section of each tissue-engaging portion is a 180 degree return bend.

7. The device defined in claim 1, in which the connecting section of each tissue-engaging portion has an upright inner portion limiting insertion of an iris edge portion.

8. The device defined in claim 7, in which the upright inner portion of the connecting section is constructed to extend diagonally across an edge portion of an iris when received in the channel.

9. The device defined in claim 7, in which the upright inner portion of the connecting section is constructed so as not to extend diagonally across an edge portion of an iris when received in the channel.

10. The device defined in claim 1, in which the strand is a length of plastic material having opposite ends joined together to form the continuous ring.

11. The device defined in claim 10, including a drop of adhesive holding the opposite ends together.

12. The device defined in claim 11, in which each of the opposite ends has an indented portion, the adhesive filing the indented portions and encircling the opposite ends adjacent to the indented portions.

13. The device defined in claim 10, in which the strand is a length of a single long strand of resilient material having opposite ends joined together to form the continuous ring, each of the opposite ends having an indented portion, and including a drop of adhesive filing the indented portions and encircling the opposite ends adjacent to the indented portions.

14. The device defined in claim 1, in which the sides are of equal length.

15. The device defined in claim 1, in which the ring is square.

* * * * *